United States Patent [19]
Kasha, Jr.

[11] Patent Number: 5,737,060
[45] Date of Patent: Apr. 7, 1998

[54] VISUAL FIELD PERIMETRY USING VIRTUAL REALITY GLASSES

[76] Inventor: John R. Kasha, Jr., 9617 Great Hills Trail, Apt. 1012, Austin, Tex. 78759

[21] Appl. No.: 696,580

[22] Filed: Aug. 16, 1996

[51] Int. Cl.$^6$ ...................................................... A61B 3/02
[52] U.S. Cl. ...................................................... 351/224
[58] Field of Search ................................. 351/222, 223, 351/224, 237, 239, 226

[56] References Cited

U.S. PATENT DOCUMENTS

| | | | |
|---|---|---|---|
| 4,349,250 | 9/1982 | Gelius | 351/32 |
| 4,798,456 | 1/1989 | Euoch et al. | 351/222 |
| 4,995,717 | 2/1991 | Damato | 351/224 |
| 5,026,151 | 6/1991 | Waltuck et al. | 351/243 |
| 5,035,500 | 7/1991 | Rorabaugh et al. | 351/226 |
| 5,565,949 | 10/1996 | Kasha | 351/224 |

Primary Examiner—Huy Mai

[57] ABSTRACT

Visual field perimetry may be performed using virtual reality glasses, a computer, a printer and an external mouse. The advantages of such a system are price, portability and patient comfort. Virtual reality glasses containing an independent display for each eye allow both eyes to be tested at once. They also allow one eye to be used for fixation while the other eye is being tested. In order to maximize the use of the small screens of virtual reality glasses a moving fixation point is used. Predefined discrete targets are placed momentarily on the screen at angles calculated based on the current location of the fixation point. Patients respond to the targets by clicking a mouse button. Fixation monitoring is handled by blind spot monitoring of both eyes or by monitoring responses to a change in direction of the moving fixation point. Results in numerical or grayscale format may be sent to a computer screen or printer.

8 Claims, 10 Drawing Sheets

VISUAL FIELD PERIMETRY USING VIRTUAL REALITY GLASSES

BACKGROUND—FIELD OF INVENTION

This invention relates to visual field perimeters, specifically to the use of virtual reality glasses and personal computers as visual field perimeters.

BACKGROUND—DESCRIPTION OF PRIOR ART

The visual field of the human eye is the entire area that is visible at any given time. Acuity or "eye chart" tests measure a small portion of the visual field called the central vision. Perimetry is the primary method of assessing the remainder of the visual field sometimes referred to as the peripheral vision. Perimetry involves fixating a patient's central vision while presenting light stimulus in their peripheral vision. By presenting large numbers of light stimuli throughout the visual field and recording the patient's reaction to these stimuli, a mapping of the visual field may be obtained.

It is particularly important to obtain visual field mappings when diagnosing and treating diseases which affect the visual field like glaucoma. Currently, most visual field mappings are obtained by machines. These machines are called automated visual field perimeters or computerized perimeters. These machines present light stimuli or targets, monitor the central vision fixation, record the reaction to targets, and map the visual field.

Computerized Perimeters

The majority of computerized perimeters are specialized pieces of hardware. They typically consist of a projection area, an embedded controller, an input device for an operating technician, an input device for the patient, and a method of printing results. These machines are built for physician's offices or hospitals. As a result they are, bulky, not portable, and usually require their own room. They are also expensive. Most computerized perimeters cost between $7000 and $23000.

The process and apparatus used by a typical computerized perimeter are described in U.S. Pat. No. 4,349,250 to Gelius (1982). The process outlined in this patent contains the general steps used by most perimeters. These steps include setting up the patient, pre-testing for an individual threshold, modifying the program based on this threshold, monitoring fixation, running the test, and displaying results. The process also contains the useful but not completely necessary step of value comparison with standard values. The apparatus detailed in this patent is specialized. Consequently, it is expensive to build and not portable.

Another drawback to most computerized perimeters is the fatiguing nature of the test. In most perimeters a patient is asked to keep their eye fixated on a stationary point for possibly more than 10 minutes. There have been many attempts to alleviate this problem. The majority of these attempts have focused on the duration of the test. Tests with fewer points and more approximations have been developed. Of course, these tests sacrifice accuracy for a reduction in total test time.

Moving Fixation

Another method introduced to reduce the fatiguing nature of computerized perimetry is a moving fixation point. A moving fixation point means that the eye would also be able to move which would significantly reduce fatigue. In U.S. Pat. No. 5,035,500 to Rorabaugh et al. (1991) a mechanism is described which allows movement of the fixation point in a visual field test. Although this mechanism may be useful in reducing test fatigue, it suffers from a number of other problems. First of all, the hardware described in this patent is highly specialized. It therefore follows that this equipment will be expensive and not portable.

Secondly, the perimeter described in this patent uses blind spot monitoring as its method of fixation control. Blind spot monitoring involves placing a target stimulus in a patient's blind spot periodically. If the patient sees the target in the blind spot it is assumed that the patient has lost fixation. If the patient does not see the target in the blind spot it is assumed that fixation has been maintained.

There are two problems with blind spot monitoring. The first problem is encountered with blind spot monitoring in general. If a patient has a large visual field defect near or surrounding the blind spot it is difficult to locate the blind spot. It is also not necessarily valid to assume that a blind spot target not seen means that fixation was maintained. The blind spot target may have fallen in the visual field defect.

The second problem encountered with blind spot monitoring results from its use with a moving fixation point. Since the blind spot is located 15 degrees from a patient's central vision, it must be possible to place a blind spot target 15 degrees from the fixation point no matter where it is on the screen. This means that is not possible to use a moving fixation point and blind spot monitoring on a small screen.

A third problem with the mechanism described in U.S. Pat. No. 5,035,500 to Rorabaugh et al. (1991) is the way in which targets are placed in relation to the fixation point. In fact, they are not actually placed. Instead, a number of targets at fixed locations from the fixation point are moved as a group with the fixation point. When a target is illuminated its actual location in the visual field of the eye is calculated. As a result, this method does not produce a uniform field of targets in the visual field of the eye. In order to obtain a uniform mapping the target values would have to be interpolated.

Another implementation of a moving fixation point, described in U.S. Pat. No. 4,995,717 to Damato (1991), addresses some of the problems of the mechanism outlined in U.S. Pat. No. 5,035,500 to Rorabaugh et al. (1991). In this implementation a personal computer is used as the visual field perimeter. Using such a general piece of hardware significantly reduces the cost, improves portability, and addresses the first problem of the previous mechanism.

In addition, the implementation described in U.S. Pat. No. 4,995,717 to Damato (1991) uses a different form of fixation control. As the fixation point moves, the patient is required to keep the fixation point surrounded by a cursor. The cursor is, of course, larger than the fixation point and is controlled by moving the mouse of the personal computer. It is assumed that fixation is maintained while the cursor is surrounding the fixation point. It is assumed that fixation is lost when the cursor is no longer surrounding the fixation point. This method of fixation control avoids the problems of the previous mechanism that were introduced by blind spot monitoring.

Although this implementation has advantages over the previous mechanism it also has problems. First of all, as with the previous mechanism, targets are placed at fixed locations with respect to the fixation point. They are then moved as a group with the fixation point. Again, this procedure results in a nonuniform mapping of the visual field.

Secondly, the method of fixation control requires that the mouse be moved continuously with the fixation point. Such movement of the mouse may be difficult for disabled or elderly people. Also, in this implementation, the patient responds to light stimulus by clicking a mouse button. As a result, test performance may be affected by the patient's ability to coordinate two manual activities involving the mouse.

Previous Application

The applicant has filed a patent application entitled "Visual field perimetry on a small computer screen" (Ser. No. 08/499,852 filed on Jul. 10, 1995). This application describes a method that can be used to perform visual field perimetry on any small computer screen in general.

The application filed on Jul. 10, 1995 differs from this application in many ways. First of all, this application declares the specific use of virtual reality glasses in its only independent claim. The application of Jul. 10,1995 spoke of a means to fixate the location of the eye with respect to the screen. Secondly, this application describes how virtual reality glasses with two displays can allow both eyes to be tested at once, follow the fixation point object and be monitored for fixation loss through blindspot testing. The application of Jul. 10, 1995 did not discuss the use of two displays.

Thirdly, because two displays may be used with virtual reality glasses, this application outlines two methods of monitoring fixation. These methods are two separate dependent claims. The application of Jul. 10, 1995 detailed only one method of monitoring fixation, and it was part of the independent claim. Finally, this application claims a method of insuring that the retina is properly illuminated before testing. The application of Jul. 10, 1995 made no similar claim.

In short, this application was filed because major improvements were made to the original invention described in the application of Jul. 10, 1995.

OBJECTS AND ADVANTAGES

Accordingly, several objects and advantages of my invention are:

(a) to provide a visual field perimeter at a lower cost;
(b) to provide a visual field perimeter that can easily be ported;
(c) to provide a visual field perimeter that can test both eyes simultaneously;
(d) to provide a visual field perimeter that can use either eye or both eyes to fixated;
(e) to provide a visual field perimeter with a test that is less fatiguing; and
(f) to provide a visual field perimeter test that places targets in a uniform field.

DRAWING FIGURES

Figure 1:
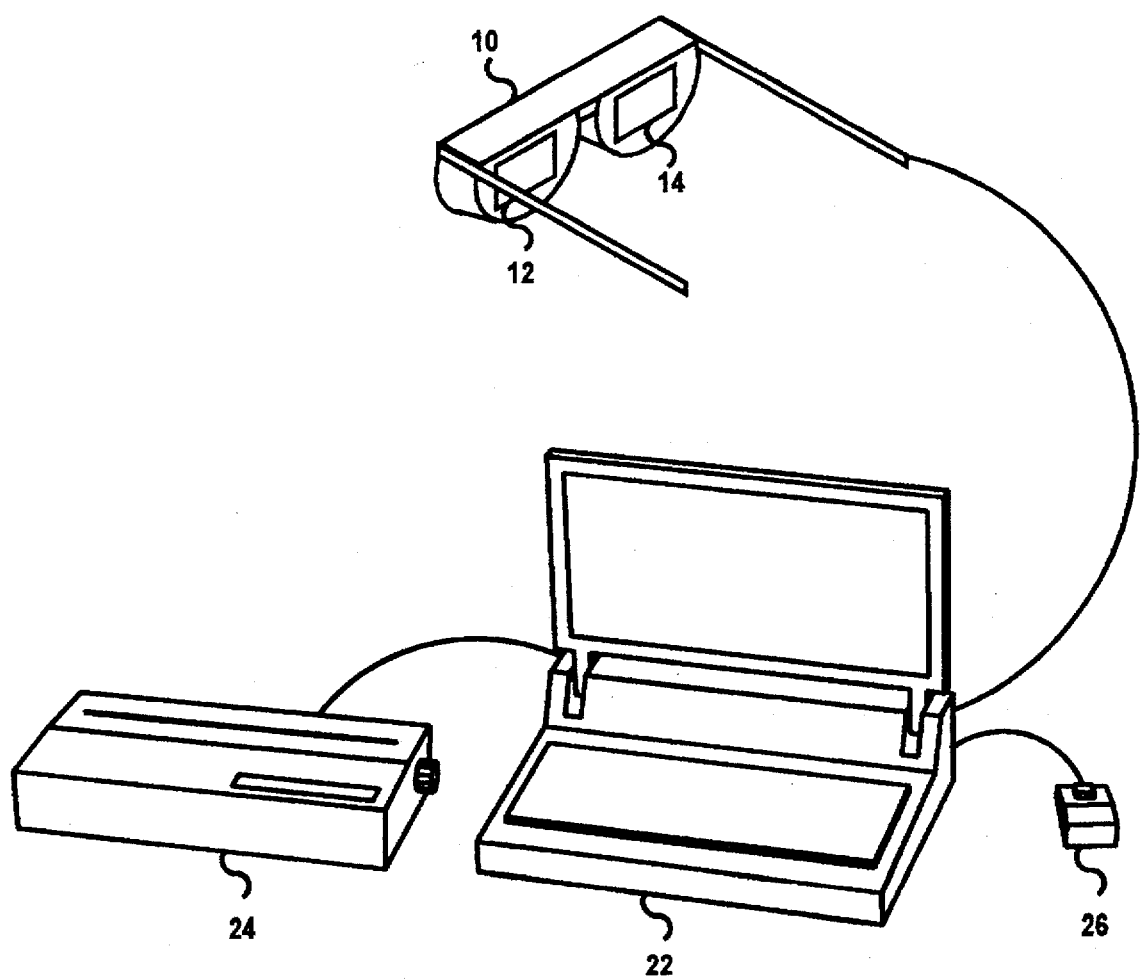
FIG. 1 shows the primary components needed to perform visual field perimetry using virtual reality glasses: virtual reality glasses, a computer, a computer mouse and a computer printer.

REFERENCE NUMERALS IN DRAWINGS 10 virtual reality glasses
12 left eye display of the virtual reality glasses
14 right eye display of the virtual reality glasses
16 discrete target
18 fixation point object
20 colored body part of fixation point object
22 computer
24 computer printer
26 computer mouse
30 path of the fixation point object
32 section boundary
34 blindspot target
38 area where targets are being shown
40 area where targets will be shown when fixation point object moves to the next section
42 horizontal retinal axis
44 vertical retinal axis Description-FIGS. 1–11

FIG. 1

A preferred embodiment of a visual field perimetry system is illustrated in FIG. 1. The four major components of the system are virtual reality glasses 10, a computer 22, a computer printer 24 and a computer mouse 26. The virtual reality glasses are used to illuminate the retina and maintain the location of the eye with respect to the illumination source. As an added benefit they allow head movement during testing.

Also, in the preferred embodiment the virtual reality glasses contain two independent displays: FIG. 1 shows the left eye display of the virtual reality glasses 12 and the right eye display of the virtual reality glasses 14. Although the physical location of these displays within the glasses and the type of optics used is unimportant. It is important, that they appear to the patient as one display located at a distance.

The computer 22 of FIG. 1 is the means by which a fixation point and discrete targets are displayed on the virtual reality glasses 10. The computer 22 runs a software program that is described in FIGS. 12–14. In addition, to controlling the virtual reality glasses 10 the computer 22 monitors the computer mouse 26 for input and can send output information to the computer printer 24. The computer also maintains a database of test results and can display test data on its display.

Figure 2:
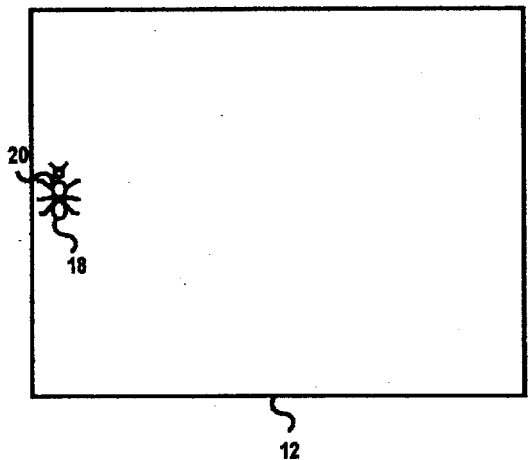
FIG. 2 shows a target being presented to the right eye display of the virtual reality glasses.
Figure 2:
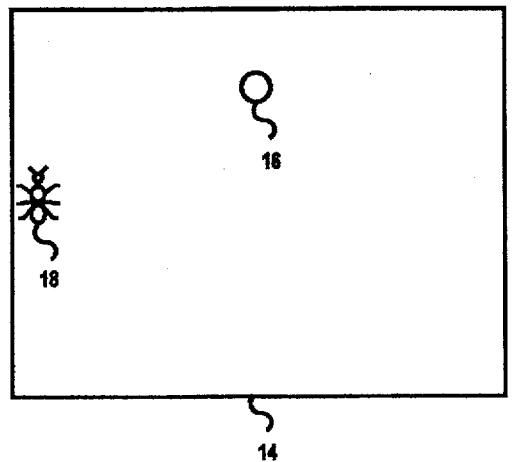
Figure 3:
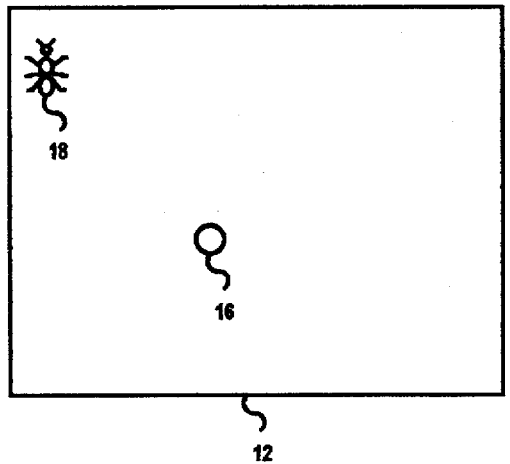
FIG. 3 shows a target being presented to the left eye display of the virtual reality glasses.
Figure 3:
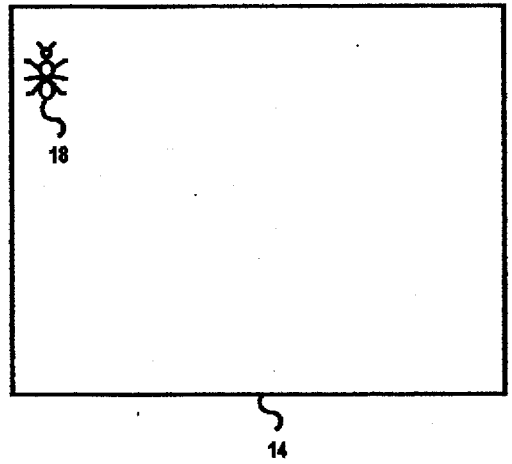

FIGS. 2 and 3

FIGS. 2 and 3 show the two displays of the virtual reality glasses, which is the preferred embodiment. There are two advantages to using two independent displays. The first advantage is that both eyes can be tested at once. This is accomplished by rendering targets to each of the two displays independently. The second advantage is that both eyes can be used for fixation. If one eye has a defect in the central vision, its field can still be tested because the other eye can be used for fixation.

The rendering of targets to both eyes independently is depicted in FIGS. 2 and 3. In FIG. 2 a discrete target 16 is rendered to the right eye display of the virtual reality glasses 14. In FIG. 3 a discrete target 16 is rendered to the left eye display of the virtual reality glasses 12 at some later time. Note that targets are never rendered to both eyes at the same time. Also, note that the patient is not able to distinguish which eye is being tested.

The rendering of the fixation point object to both eyes is similarly depicted in FIGS. 2 and 3. The left eye display of the virtual reality glasses 12 contains the fixation point object 18. The fixation point object 18 has the shape of an ant in order to make the test more interesting. In addition, the legs of the ant are animated as the ant moves so that the ant appears to walk around the screen.

In order to maintain fixation in a single spot, the fixation object is given a colored body part 20. The patient is then asked to focus on this colored body part 20 throughout the test.

The right eye display of the virtual reality glasses 14 in FIG. 2 also contains the fixation point object 18. The fixation point object 18 in this display is identical to the fixation point object 18 in the display of left eye. In fact, both fixation points are rendered in the same location. To the patient it appears that there is one screen and one ant walking around that screen. FIG. 3 shows the fixation point object 18 at some later time.

Figure 4:
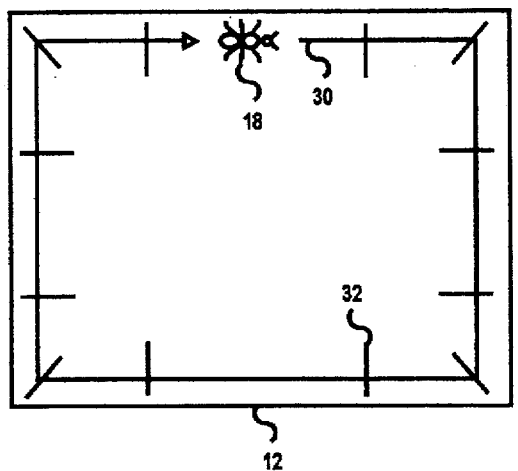
FIG. 4 shows the fixation point object moving to the right within a section of the screen.
Figure 4:
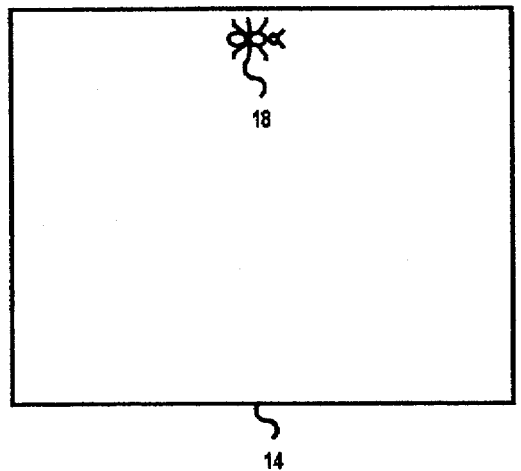
Figure 5:
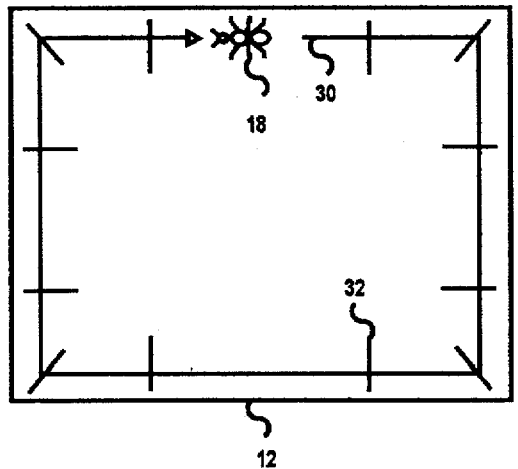
FIG. 5 shows the fixation point object moving to the left within a section of the screen.
Figure 5:
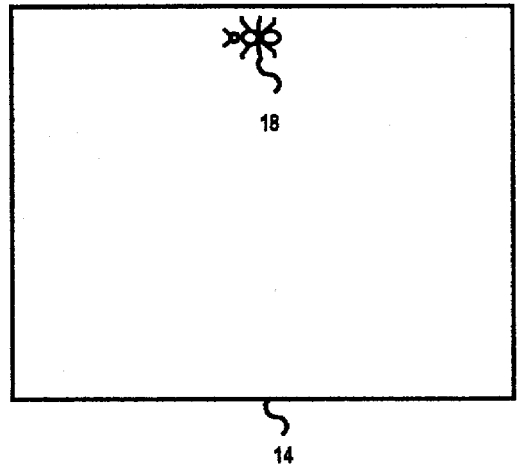

FIGS. 4 and 5

The movement of the fixation point object 18 is more clearly shown in FIGS. 4 and 5. The fixation point is moved around the screen in order to maximize the use of the screen. The way in which the fixation point is moved around the screen, or its path, insures that the parts of the retina to be tested are properly illuminated with the background light intensity before they are tested.

FIGS. 4 and 5 show the left eye display of the virtual reality glasses 12 and the right eye display of the virtual reality glasses 14. Both Figs. also show the fixation point object 18. In addition, the left eye display of the virtual reality glasses 12 in both Figs. shows the overall path of the fixation object 30 and the 12 sections the fixation point object 18 must traverse. The 12 sections the fixation point object must traverse are bounded by 12 section boundaries 32.

The overall direction of movement of the fixation point around the screen is clockwise, as shown by the path of the fixation object 30. This continuous overall path insures the proper illumination of the retina before testing. This is more easily seen in FIGS. 8 and 9.

The path of the fixation point is divided into 12 sections in order to maximize the use of the screen. The 12 sections actually correspond to 12 groups of targets. When the fixation point is in a certain section, the targets of the corresponding group will be shown on the screen. This insures that the targets will be seen on the screen, since the majority of targets are off of the screen at any one time.

Within a section the fixation point may move in either direction toward either boundary. Note that in FIG. 4 the fixation point object 18 is moving in the top central section to the right. At some time later, the fixation point object 18 is moving in the top central section to the left as depicted in FIG. 5.

At either boundary of a section the fixation point will simply change direction to stay within the section. The fixation point will cross the boundary and move on to the next section once all of the targets of the section's corresponding group have been shown. Note that the fixation point object 18 traverses the overall path of the fixation point 30 only once.

The testing software of the virtual reality glasses perimeter has two methods of monitoring fixation. In the first method, the direction of the fixation point object 18 is changed randomly within a section as shown in FIGS. 4 and 5. The patient must then respond to the change in direction by using the computer mouse 26 shown in FIG. 1. The patient must also respond to the direction changes at the boundaries. Any change in direction which the patient does not respond to is considered a fixation loss.

There are two advantages to this fixation monitoring technique. First of all, either eye can be used for fixation. Secondly, the patient must concentrate on the movements of the fixation point, so fixation is more likely to be maintained. The drawback to this technique is that the patient must think about the direction of the fixation point and the presence of targets and respond to both. Note that targets are never presented while the fixation point is changing direction.

Figure 6:
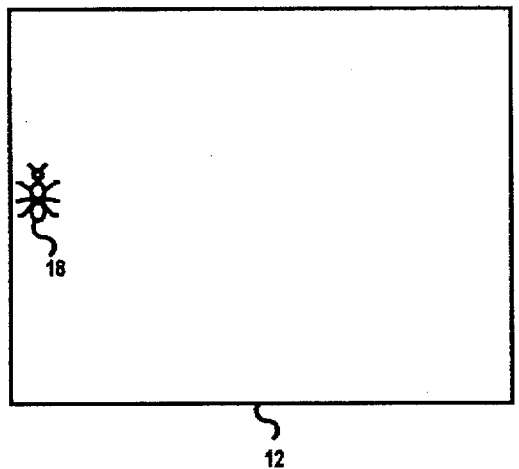
FIG. 6 shows a blindspot target being presented to the right eye display of the virtual reality glasses.
Figure 6:
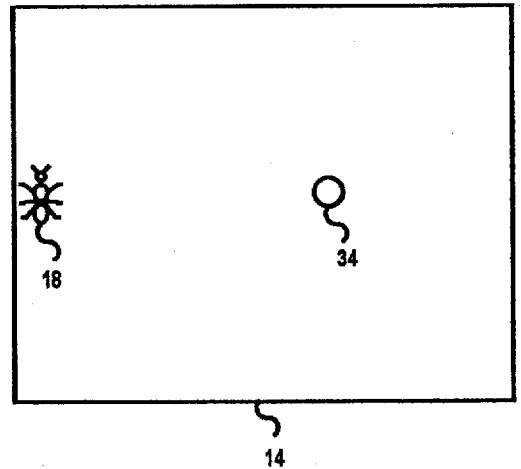
Figure 7:
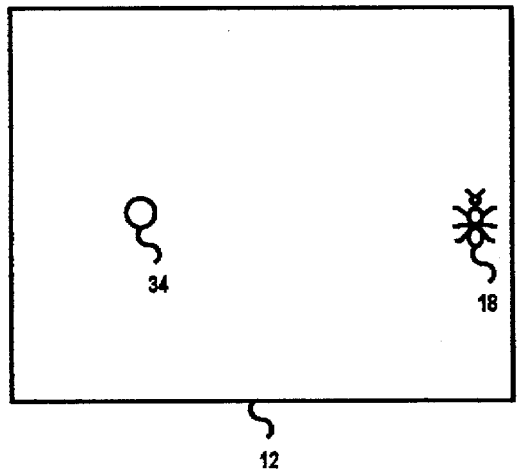
FIG. 7 shows a blindspot target being presented to the left eye display of the virtual reality glasses.
Figure 7:
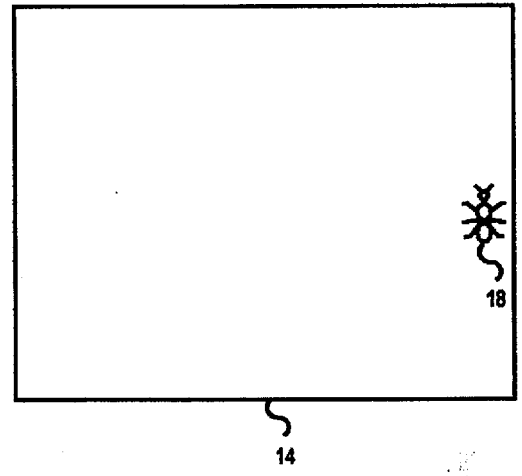

FIGS. 6 and 7

The second method of fixation monitoring is made possible through the two independent displays of the preferred embodiment. Because there are two displays the blindspot for at least one eye is almost always available for testing.

Blindspot monitoring of both eyes is shown in FIGS. 6 and 7. In FIG. 6 a blindspot target 34 is displayed on the right eye display of the virtual reality glasses 14 while the fixation point object 18 is in the left portion of the screen. When the fixation point object 18 is in the right portion of the screen a blindspot target 34 can be displayed on the left eye display of the virtual reality glasses 12, as shown in FIG. 7.

If the a patient responds to a blindspot target, it is considered to be a fixation loss. In other words, blindspot targets should not be seen. As in the case of movement fixation monitoring, the computer mouse 26 is monitored during and after a blindspot target is displayed in order to determine if there is a fixation loss.

The advantage of blindspot monitoring is that it places no additional demands on the patient. It does, however, have two disadvantages. First of all, it requires that the blindspots of both eyes be located and used. Secondly, even with two displays the blindspots of either eye will not always be available for testing. In particular, when the fixation point is at the center top or center bottom of the screen blindspot monitoring may not be possible depending on screen size.

Figure 8:
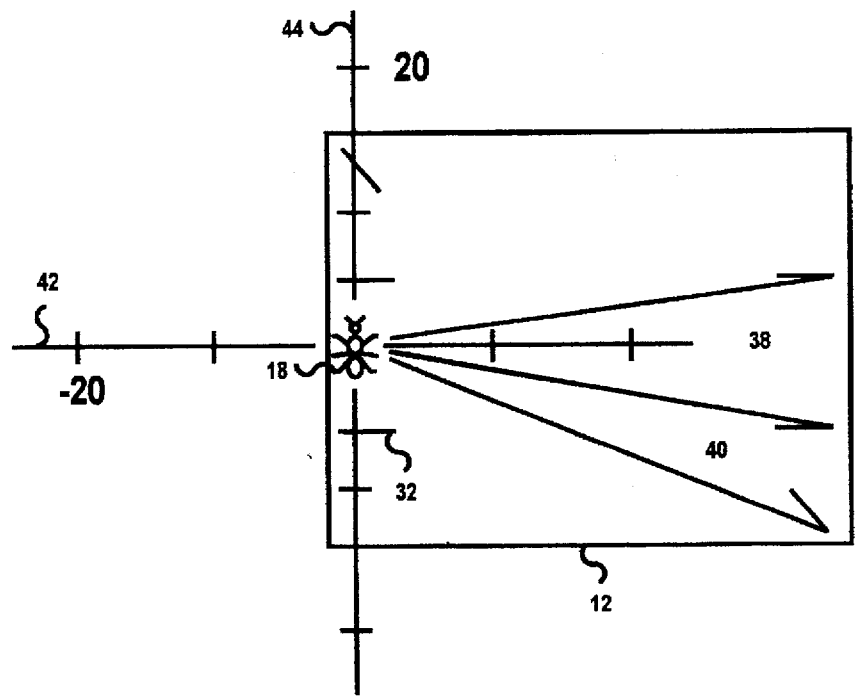
FIG. 8 shows the how the screen of the left eye display covers an area of the retina when the fixation point object is located in the central section on the left hand side of the screen.
Figure 9:
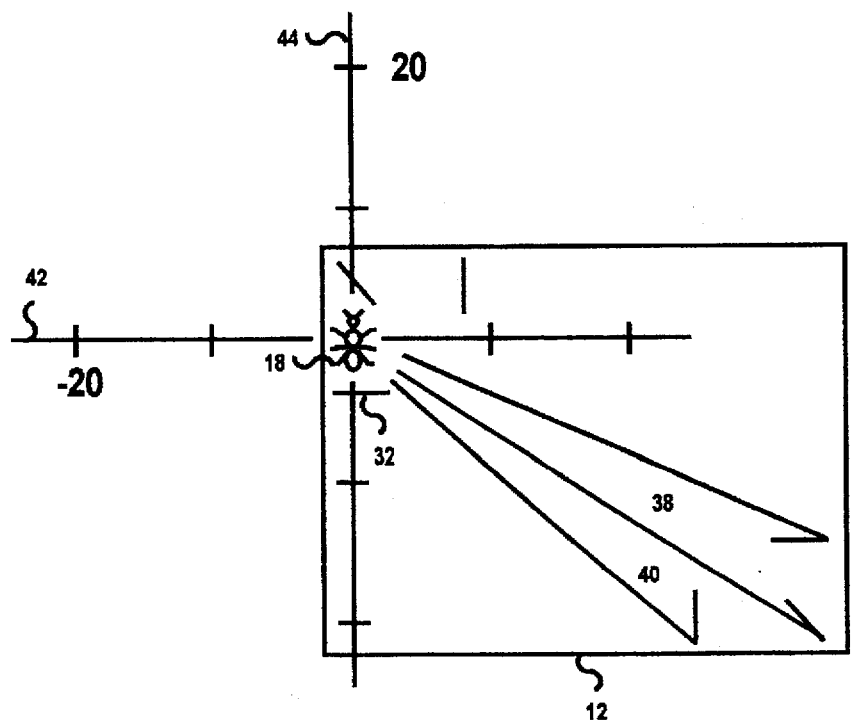
FIG. 9 shows the how the screen of the left eye display covers an area of the retina when the fixation point object is located in the top section on the left hand side of the screen.

FIGS. 8 and 9

FIGS. 8 and 9 depict the movement of the left eye display of the virtual reality glasses 12 over the retina as the eye follows the movement of the fixation point object 18. The effect is the same for the right eye and right eye display. As long as fixation is maintained the fixation point object 18 stays in the central vision. This is shown in FIGS. 8 and 9 by maintaining the fixation point object 18 at the origin of the horizontal retinal axis 42 and the vertical retinal axis 44.

The entire left eye display of the virtual reality glasses 12 is illuminated at a uniform intensity in order to stimulate the retina before testing. Targets are then shown on the display at intensities above the background intensity.

FIG. 8 shows the fixation point object 18 in the left central section of the left eye display of the virtual reality glasses 12. FIG. 9 shows the fixation point object 18 at some time later in the left top section of the left eye display of the virtual reality glasses 12. Note how the left eye display of the virtual reality glasses 12 changes position from FIG. 8 to FIG. 9. Thus, as the fixation point object 18 moves in clockwise fashion around the left eye display of the virtual reality glasses 12, the illuminated left eye display of the virtual reality glasses 12 moves in a likewise clockwise fashion over the retinal axes. Also, since the path of the fixation point is continuous between sections, the illumination of the retina by the display moving over it is also continuous between sections.

As the fixation point object 18 moves within a section the left eye display of the virtual reality glasses 12 the display will also move over the retina in either direction. The overall retinal path, however, is continuously illuminated due to the division of the display into sections. This is illustrated in FIG. 8. Notice that as fixation point object 18 moves within the left central section and the left eye display of the virtual reality glasses 12 moves correspondingly over the retina, the area where targets are to be shown 38 of the retina will always be illuminated by the display.

Also notice in FIG. 8, that the area where targets will be shown when fixation point object moves to the next section 40 will also be illuminated before that area is tested. This is clearly shown as the fixation point moves between sections as shown in FIGS. 8 and 9. The area where targets will be shown when fixation point object moves to the next section 40 of FIG. 8 becomes the area where targets are to be shown 38 of FIG. 9.

Finally, it is important to note that targets are initially grouped according to a calculation based on the fixation point being located at the center of the display. At test time, however, the location of targets are calculated based on the actual location of the fixation point on the display. As a result, the targets may be slightly outside of the predefined area. Again, the use of sections much smaller than the display insures that targets will be shown on the screen.

Figure 10:
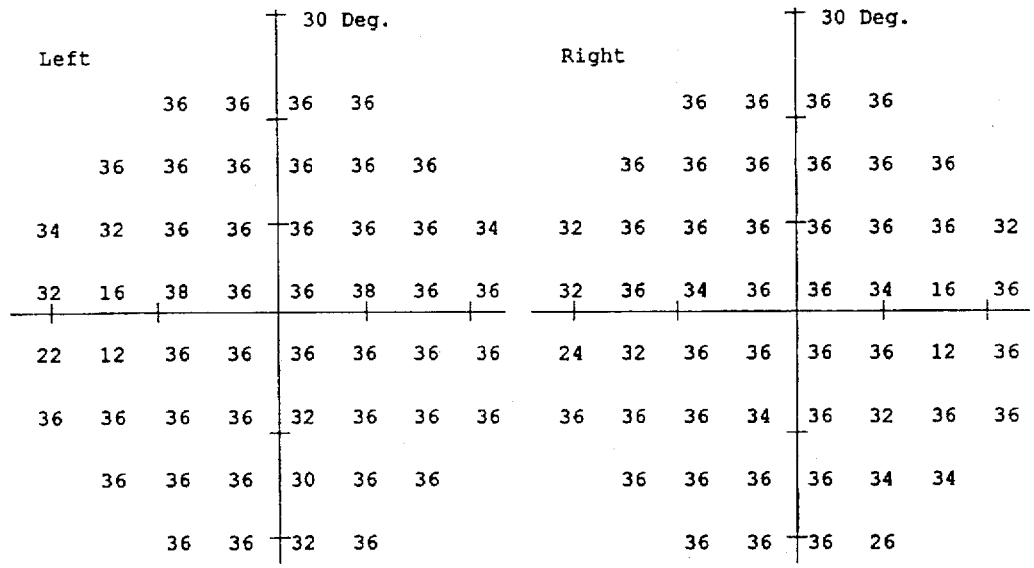
FIG. 10 is an example of printed numerical data from a visual field test.
Figure 11:
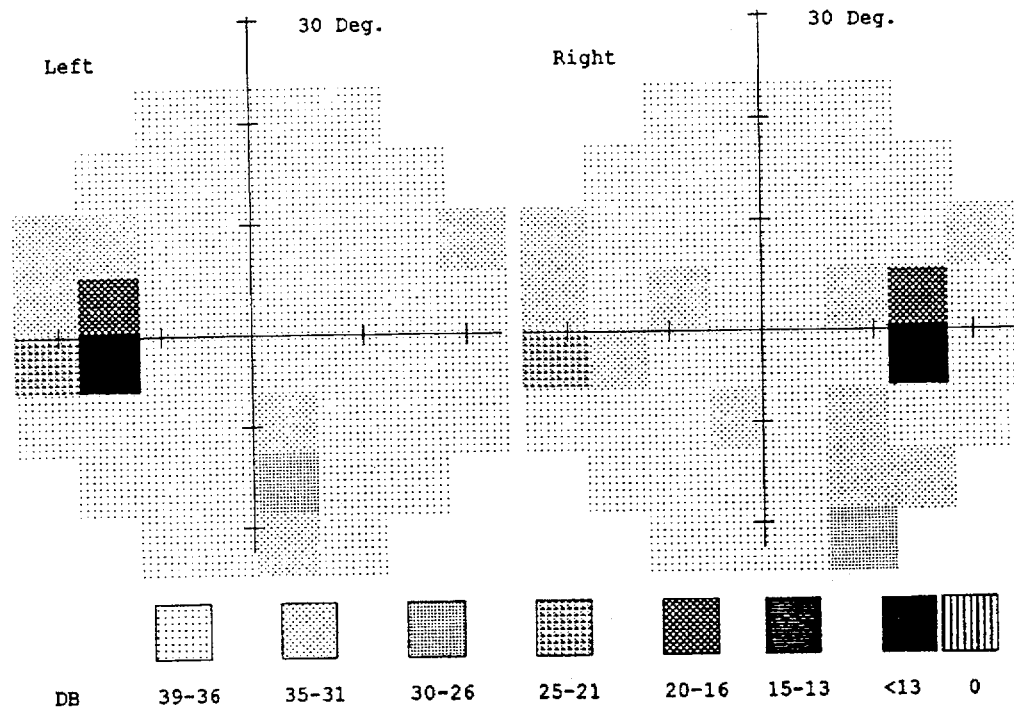
FIG. 11 is an example of printed grayscale data from a visual field test.

FIGS. 10 and 11

As mentioned earlier, the testing software is able to show the results of a test on the display of the computer 22 shown in FIG. 1 or send these results to the computer printer 24 of FIG. 1. The two types of printed results available from the testing software are shown in FIGS. 10 and 11.

Both types of printed results show patient and overall test information at the top of the page. They do, however, differ in how they display the values recorded at target locations. The printed results of FIG. 10 are in numerical format. The actual light intensity value (in decibels, DB) of the target seen at a particular location is printed in numerical format at that location. In addition, a key is provided expressing the decibel and corresponding apostilbs (ASB) ranges.

The printed results of FIG. 11 are in grayscale format. A grayscale shading of the decibel range of the target seen at a particular location is printed at that location. The key for the grayscale format and decibel (DB) range is printed at the bottom of the page.

Figure 12:
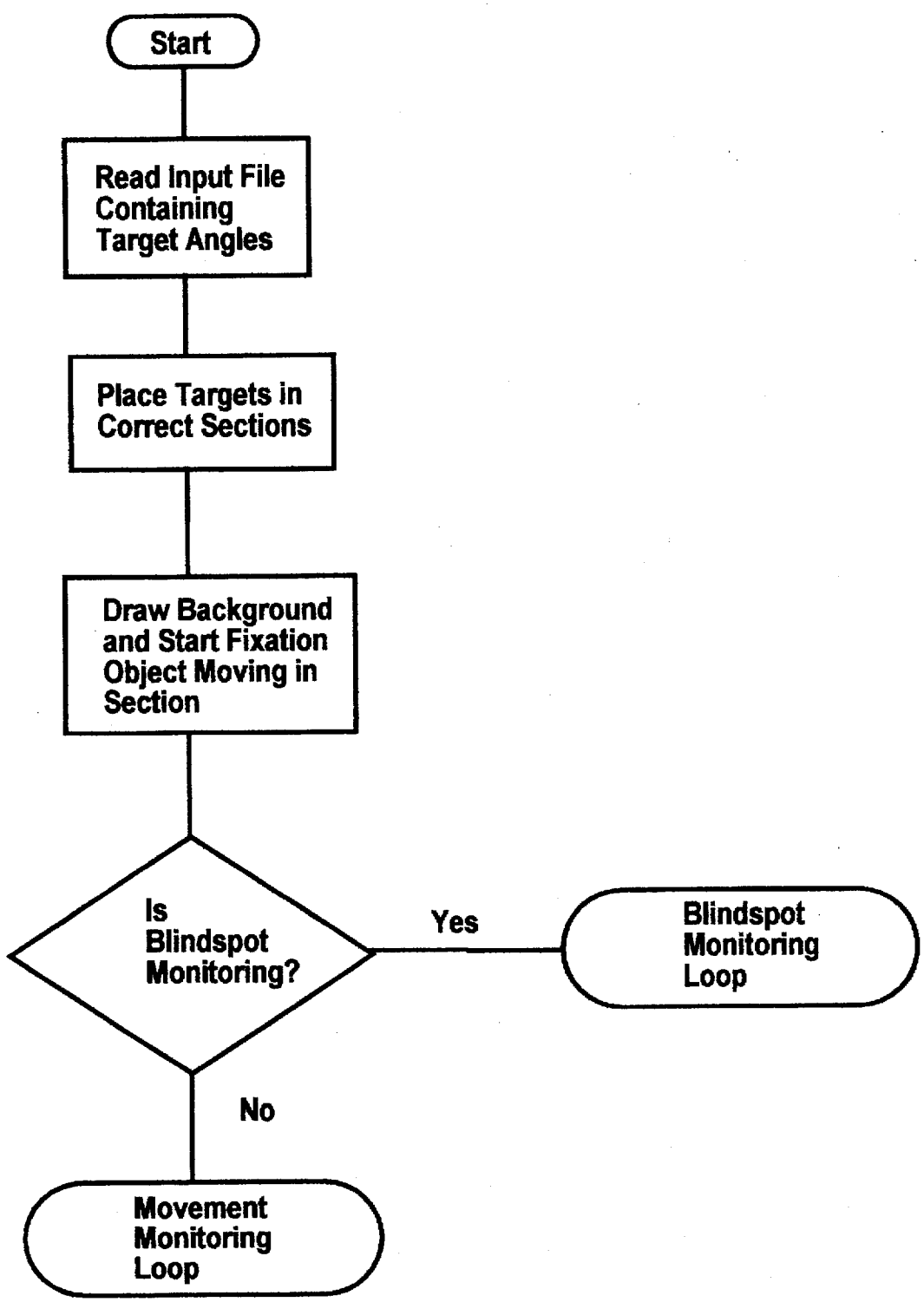
FIG. 12 is a flow chart showing the initial steps of the testing software.
Figure 13:
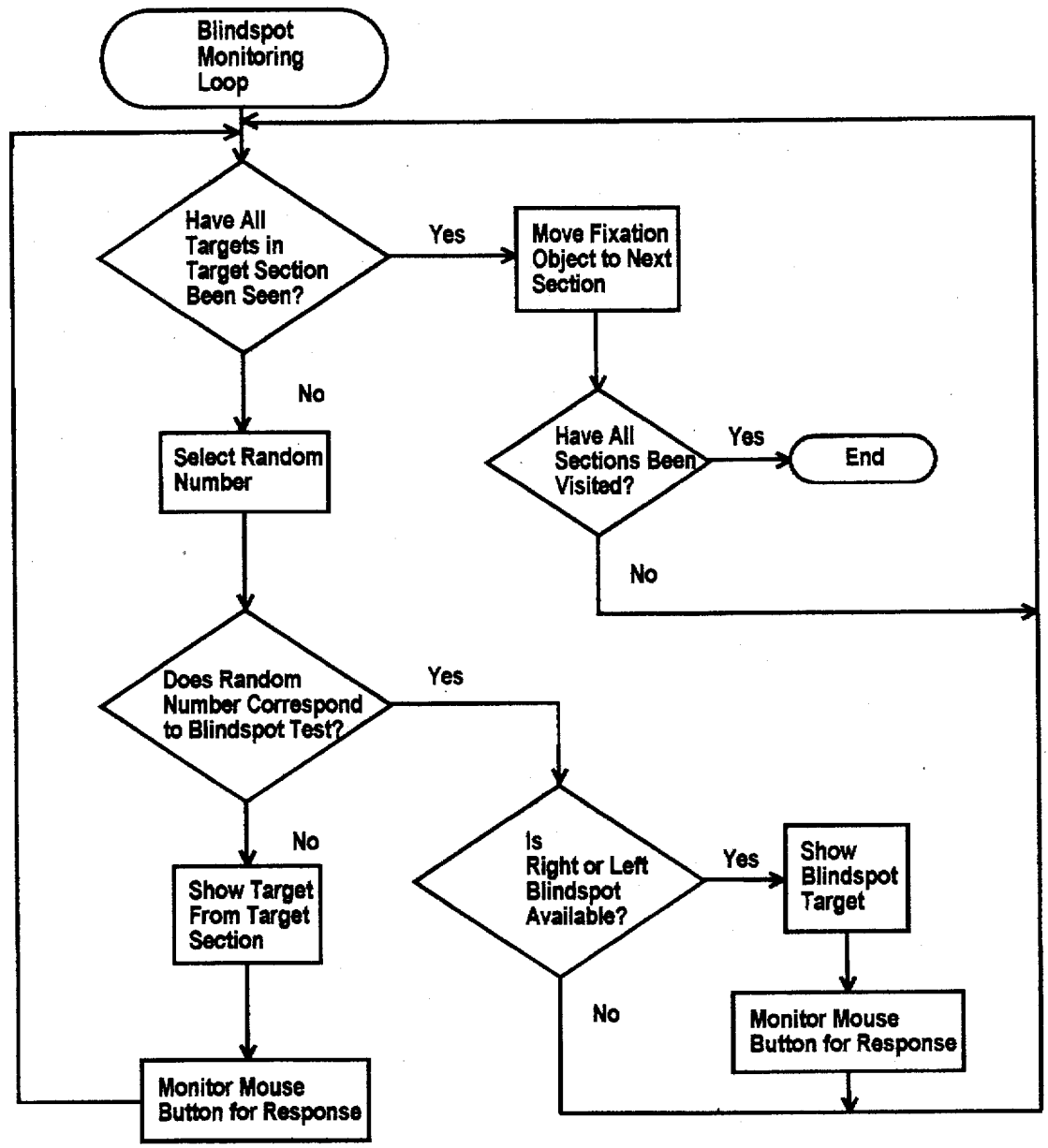
FIG. 13 is a flow chart showing the blindspot monitoring loop of the testing software.
Figure 14:
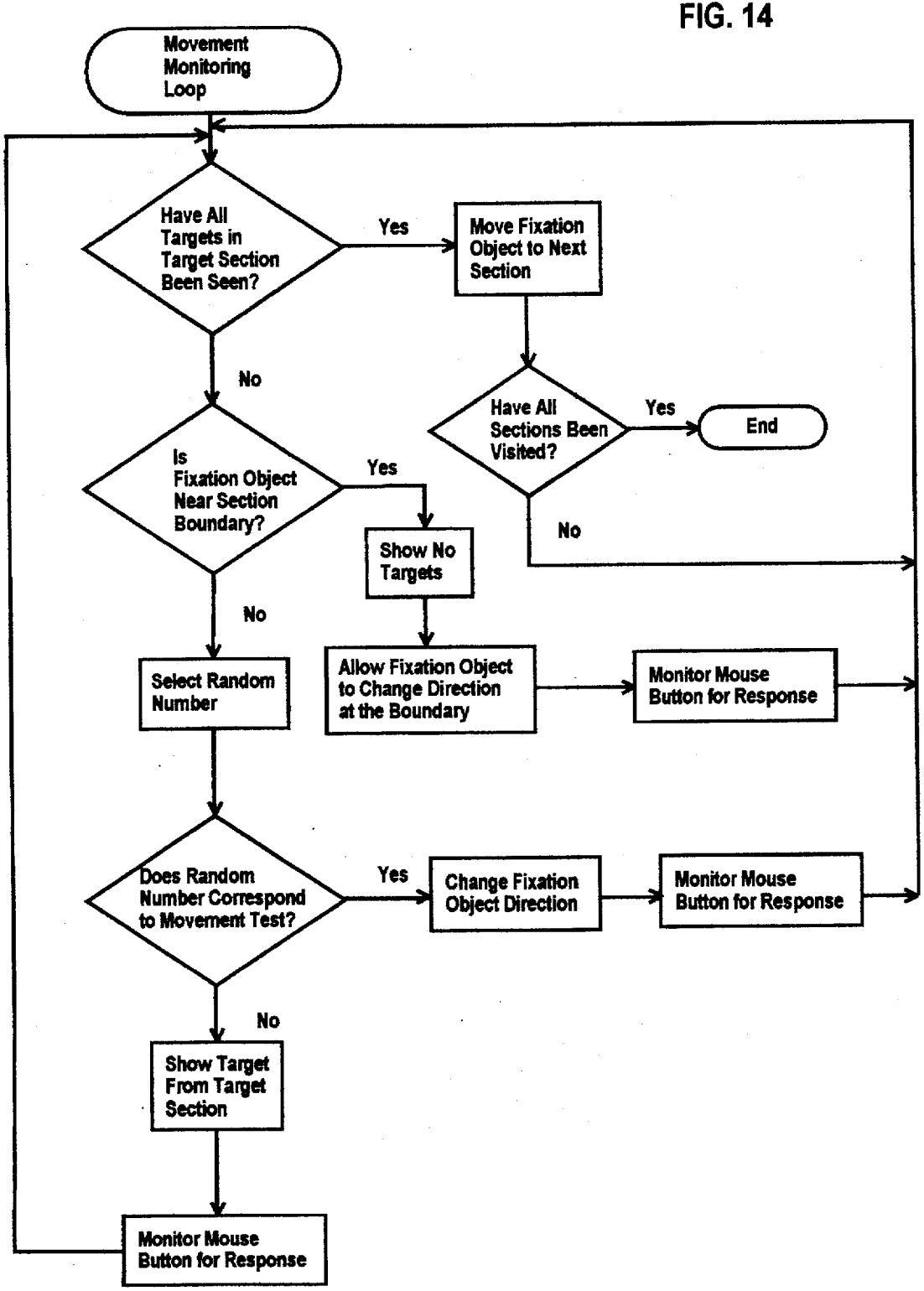
FIG. 14 is a flow chart showing the movement monitoring loop of the testing software.

Program Operation—FIGS. 12–14

The preferred software used to produce a visual field test using virtual reality glasses is outlined in FIGS. 12–14.
Initialization The initialization of the preferred software is diagrammed in FIG. 12. On initialization an input file is read which contains patient information and test parameters. This file defines the test. In the input file, targets are defined by specifying the eye to be tested and two angles. The first angle is the angle of the target from the fixation point with respect to the eye. The second angle is the angle from the horizontal of the retinal axis.

After reading the input file, the targets are divided into sections corresponding to sections the fixation point will traverse. The targets are placed in these sections by calculating the locations of the targets if the fixation point were in the center of the screen. The calculation uses the two angles provided in input file, the optical location of the eye with respect to the virtual reality glasses, the optical dimensions of the virtual reality glasses and the optical location of the fixation point.

A uniform background intensity is then drawn to the screen. Additionally, the fixation point object is draw in its starting section. The test is begun by a mouse button click from the patient. When this click is received, the fixation point starts moving within the starting section.

At this point the software is in one of two similar loops depending on the type of fixation monitoring that was found in the input file. If blindspot monitoring was selected in the input file, then the program enters the Blindspot Monitoring Loop. If the fixation point movement change type of monitoring was selected in the input file, then the program enters the Movement Monitoring Loop.

Blindspot Monitoring Loop

The Blindspot Monitoring Loop is diagrammed in FIG. 13. The first question asked in this loop is if all the targets of the group corresponding to the section currently occupied by the fixation point have been shown. If they have not, the program prepares to show a target.

In addition to showing a target, however, it must determine if it is time to check the patient's fixation. It does this by generating a random number. If that random number falls in the frequency range specified in the input file for fixation testing, then the program will attempt to test the blindspot. If the random number falls outside of the fixation check frequency range a test target is shown.

If a test target is to be shown, it is selected from the group of targets corresponding to the section of the fixation point. The location of the test target is calculated based on the current location of the fixation point. As in the initialization, this calculation uses the two angles provided in the input file, the optical location of the eye with respect to the virtual reality glasses, the optical dimensions of the virtual reality glasses and the optical location of the fixation point. However, when the fixation point is not in center of the screen, the geometry is more complex. The same calculation is made as if the fixation point were at the center of a different screen. The target location is then found on the actual screen by geometrically projecting the target onto that screen. As a result, the target actually moves with the fixation point. The target is, however, only shown momentarily.

During and after the target is shown the mouse button is monitored for a response to the target. If a button click is received the target is marked as seen. If the no click is received after a certain duration, the target is marked as unseen.

Depending on the type of testing and/or the response, the target is now either removed from or returned to the target group for the section. In suprathreshold testing the target is only shown once and then removed from the group. In full threshold testing the target is shown until it reaches a maximum intensity not seen or a minimum intensity that is seen. In any event, the loop returns after a random delay to the question about the number of targets left for a section.

If a blindspot target is to be shown after random number testing, it must first be determined if either display of the virtual reality glasses is over a blindspot. If the blindspot is not available, neither a blindspot target nor a test target is shown, and the loop returns to the number of targets left for a section question.

If a blindspot is available, the program calculates the location of the blindspot and places a target at that location at an intensity given in the input file. The blindspot target also moves with the fixation and is shown momentarily like the test target. In addition, the mouse button is also monitored during and after a blindspot target is shown. If no button click is received, it is counted as a fixation loss.

After a blindspot target is shown there is a random delay, and the loop returns to the number of targets left for a section question.

If there are no more targets to be shown for the section currently occupied by the fixation point, the fixation point attempts to move to the next section. First, however, it checks to determine if all sections have been traversed. If they have, the loop is exited.

If all sections have not yet been traversed, then the fixation point moves on to the next section and the loop is continued.

Movement Monitoring Loop The Movement Monitoring Loop is diagrammed in FIG. 14. It is identical to the Blindspot Monitoring Loop except for an additional question, the way in which fixation is monitored and the interpretation of fixation responses.

The additional question asked is whether or not the fixation point is near a section boundary. Since the fixation point changes direction at a section boundary, this change must be monitored for a patient response.

If the fixation point is near a boundary no targets can be shown. The patient is never presented with both a direction change and a test target. The fixation is then allowed to change direction. The mouse button is monitored for a click during and after the fixation direction change. After a random delay the loop is continued.

In this loop, fixation is monitored by the response to changes in the fixation point's direction of movement. As a result, the fixation point's direction must be changed at random intervals. So, after selecting a random number and finding it in the fixation monitoring frequency range, the direction of the fixation point is changed. As with the direction change at the boundaries, the mouse button is monitored during and after the change for a click.

Note that interpretation of the responses from movement monitoring is opposite that of blindspot monitoring. In movement monitoring good fixation would imply that all fixation checks are seen. In blindspot monitoring good fixation would imply that all fixation checks are not seen.

End

The ends of the Blindspot and Movement Monitoring Loops are not the end of the testing software program. The program saves results to a file which may be used as a database. The results may also be retrieved from this file at the time of testing or at some later time for display on the computer or to be sent to a printer.

SUMMARY, RAMIFICATIONS, AND SCOPE

Accordingly, the reader will see that the invention of visual field perimetry using virtual reality glasses will reduce the cost and fatiguing nature of visual field tests. Additional advantages of this inventions are:

- the ability to test both eyes at the same time;
- the use of both eyes to fixate which will make the test more reliable;
- a portable visual field test that can easily be transported to schools, nursing homes, or even third world countries; and
- a perimeter that is easy to setup and use.

Although the description above contains many specificities, these should not be construed as limiting the scope of the invention but as merely providing illustrations of some of the presently preferred embodiments of this invention. Thus the scope of the invention should be determined by the appended claims and their legal equivalence, rather than the examples given.

I claim:

1. A visual field perimeter, comprising:

(a) virtual reality glasses, (b) means for displaying a fixation point and sequential discrete targets to each eye separately on said virtual reality glasses, (c) input means operable by a patient so as to record whether or not said patient sees each of said discrete targets, and (d) means for recording the relative locations of said discrete targets and whether or not said discrete targets were seen by said patient.

2. The visual field perimeter of claim 1 wherein said virtual reality glasses contain separate displays for each eye and said discrete targets may be rendered independently to each of the said displays.

3. The visual field perimeter of claim 1 wherein said discrete targets are placed momentarily on said virtual reality glasses at locations calculated from predefined angles, the optical location of the eye with respect to said virtual reality glasses, the optical dimensions of said virtual reality glasses and the optical location of said fixation point.

4. The visual field perimeter of claim 1 wherein said fixation point is moved on said virtual reality glasses so as to maximize the said predefined angles that may be tested with said virtual reality glasses.

5. The visual field perimeter of claim 1 wherein said fixation point is noticeably changed so as to maintain the attention of said patient.

6. The visual field perimeter of claim 5 further including input means operable by said patient so as to register whether or not said patient sees said noticeable change in said fixation point.

7. The visual field perimeter of claim 2 further including blindspot monitoring means of both eyes.

8. The visual field perimeter of claim 1 further including means to insure that the portion of retina to be tested is illuminated at the background light intensity for at least 5 seconds before said portion of the retina is tested.

* * * * *